(12) United States Patent
Green et al.

(10) Patent No.: US 8,268,369 B2
(45) Date of Patent: Sep. 18, 2012

(54) COMPOSITIONS AND METHODS FOR TREATING HYPERCHOLESTEROLEMIA USING ORTANIQUE PEEL EXTRACT

(75) Inventors: Curtis O. Green, St. Catherine (JM); Helen N. Asemota, Kingston (JM)

(73) Assignee: The University of the West Indies, Kingston (JM)

( * ) Notice: Subject to any disclaimer, the term of this patent is extended or adjusted under 35 U.S.C. 154(b) by 0 days.

(21) Appl. No.: 13/018,679

(22) Filed: Feb. 1, 2011

(65) Prior Publication Data

US 2011/0124722 A1    May 26, 2011

Related U.S. Application Data

(62) Division of application No. 12/504,956, filed on Jul. 17, 2009, now abandoned.

(60) Provisional application No. 61/081,916, filed on Jul. 18, 2008.

(51) Int. Cl.
*A61K 36/752* (2006.01)
(52) U.S. Cl. ...................... 424/736; 424/777
(58) Field of Classification Search .................. None
See application file for complete search history.

(56) References Cited

U.S. PATENT DOCUMENTS

| 2002/0006953 A1* | 1/2002 | McGill et al. ............... 514/453 |
| 2004/0152641 A1 | 8/2004 | Guthrie et al. |
| 2010/0015255 A1 | 1/2010 | Green et al. |

OTHER PUBLICATIONS

Green, Curtis O. et al. Determination of Polymethoxylated Flavones in Peels of Selected Jamaican and Mexican Citrus (*Citrus* spp.) Cultivars by High-Performance Liquid Chromatography. *Biomedical Chromatography*. 2007. 21, 48-54. 7 pages.

Li et al. Hydroxylated Polymethoxyflavones and Methylated Flavonoids in Sweet Orange (*Citrus sinensis*) Peel. *Journal of Agricultural and Food Chemistry*. Department of Food Science, Rutgers Univeresity. 2006. 54, 4176-4185. 10 pages.

Malterud, Karl E. et al. Inhibitors of 15-Lipoxygenase from Orange Peel. *Journal of Agricultural and Food Chemistry*. 2000. 48, 5576-5580. 5 pages.

* cited by examiner

*Primary Examiner* — Susan Hoffman
(74) *Attorney, Agent, or Firm* — Wilmer Cutler Pickering Hale and Dorr LLP

(57) ABSTRACT

The invention relates to compositions and methods for treating hypercholesterolemia, including methods for increasing HDL cholesterol levels, using a composition comprising an extract from the Ortanique peel. The invention also relates to compositions and methods for treating hypercholesterolemia, including methods for increasing HDL cholesterol levels, using a composition comprising substantially similar amounts of tetramethylscutellarein and nobiletin by weight and/or a composition comprising substantially similar amounts of tetramethylscutellarein, nobiletin, and tangeretin by weight.

8 Claims, 1 Drawing Sheet

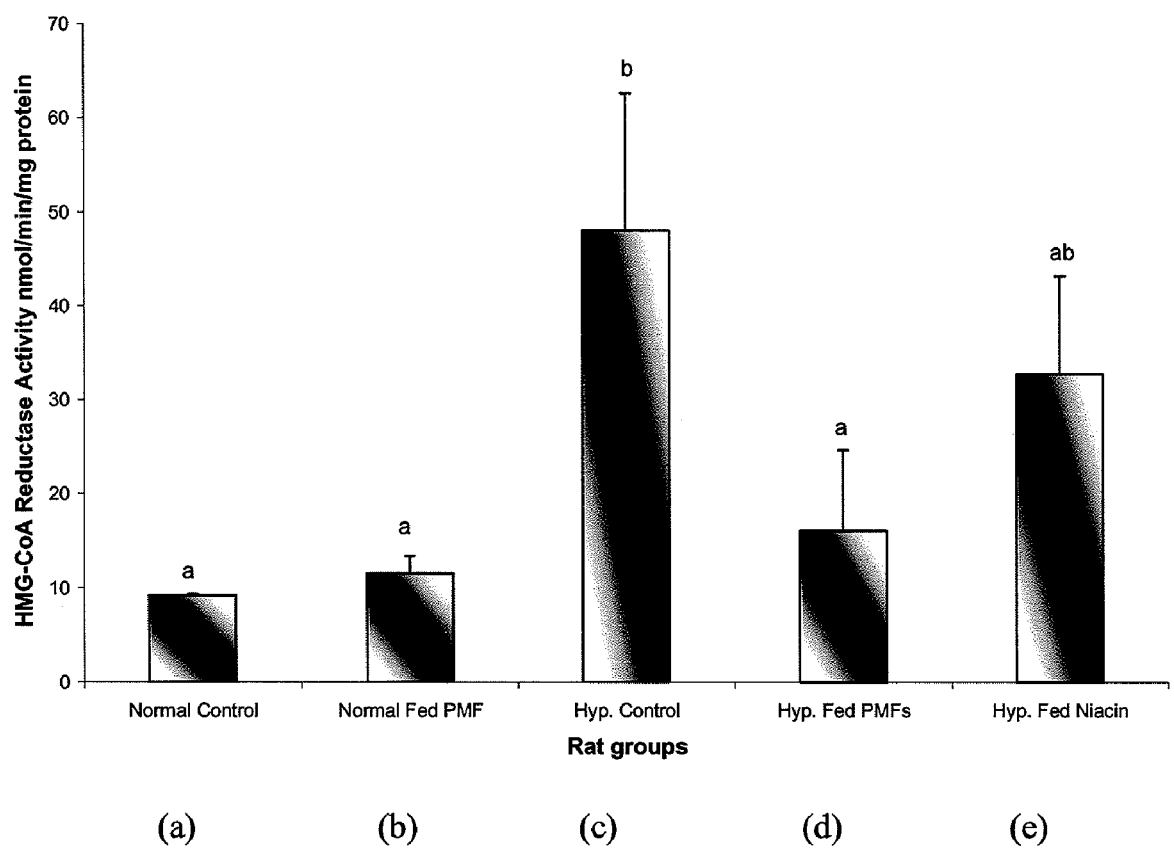

COMPOSITIONS AND METHODS FOR TREATING HYPERCHOLESTEROLEMIA USING ORTANIQUE PEEL EXTRACT

1. REFERENCE TO RELATED APPLICATIONS

This application is a division of U.S. patent application Ser. No. 12/504,956, filed Jul. 17, 2009, now abandoned, which claims the benefit of priority to U.S. Provisional Patent Application Ser. No. 61/081,916, filed Jul. 18, 2008, the entire disclosures of which are incorporated by reference herein in their entirety.

2. FIELD OF THE INVENTION

The present invention relates generally to treatment and prevention of hypercholesterolemia.

3. BACKGROUND OF THE INVENTION

Familial hypercholesterolemia affects approximately 1 in 500 people worldwide, and the elevated serum cholesterol concentrations associated with it contributes more than 50% to the risk of fatal or non-fatal coronary heart disease by age 50 in men, and at least 30% in women aged 60 and above. The prevalence of hypercholesterolemia in Jamaica is estimated at 31%. It is estimated that about 37%, or 101 million people in the United States suffer from hypercholesterolemia.

Hypercholesterolemia is implicated in many cardiovascular diseases affecting people worldwide and pose tremendous burden on the global healthcare system. In the last decade cardiovascular disease (CVD) has become the leading cause of death across the Caribbean and accounted for 19% of deaths overall in 1995. The World Health Organization report also states that coronary heart disease burden is projected to rise from around 47 million DALYs (disability-adjusted life years) globally in 1990 to 82 million DALYs in 2020 (WHO, 2004).

The major conventional drugs used to treat hypercholesterolemia include the statins (lovastatin, pravastatin, simvastatin, etc.) and niacin (nicotinic acid). Although these drugs are effective in lowering serum cholesterol levels, they cause several adverse effects. Statins, for example, cause gastrointestinal upset, muscle aches, and hepatitis. Rarer problems associated with statins include myopathy (defined as muscle pain with serum creatine kinase concentrations of more than 1000 U per liter), rash, peripheral neuropathy, and insomnia. Niacin can cause adverse effects such as flushing, abdominal pain, vomiting, headache, or elevated serum aminotransferase levels indicating liver damage.

Flavonoids are a ubiquitous family of phytochemicals that exhibit a broad spectrum of pharmacological properties. Polymethoxylated flavones are flavonoids that are almost exclusive to citrus peels and display potent anti-hypercholesterolemic, anti-cancer, anti-atherosclerotic and anti-diabetic properties.

Jamaica is the leading producer of citrus in the Caribbean. A vast majority of the citrus fruits that are harvested are used for citrus juice production, which results in large quantities of citrus peel and other citrus byproducts which end up in river beds and constitute environmental problems.

4. SUMMARY OF THE INVENTION

The invention is based, in part, on the discovery that the Ortanique peel extract is effective in treating hypercholesterolemia without the side effects of existing drugs, such as statins and niacin, and in part, on the discovery that the Ortanique peel extract is more effective in treating hypercholesterolemia compared to peel extracts from other citrus fruits.

In one aspect, the invention provides a method for reducing LDL cholesterol level in a subject comprising administering to a subject in need thereof an effective amount of a composition comprising a polar solvent soluble extract from Ortanique peel, wherein the reduction of LDL cholesterol level is observed relative to the subject before administration of the composition.

In another aspect, the invention provides a method for increasing HDL cholesterol level in a subject comprising administering to a subject in need thereof an effective amount of a composition comprising a polar solvent soluble extract from Ortanique peel, wherein the increase of HDL cholesterol level is observed relative to the subject before administration of the composition.

In one aspect, the invention provides a method for reducing total cholesterol level in a subject comprising administering to a subject in need thereof an effective amount of a composition comprising a polar solvent soluble extract from Ortanique peel, wherein the reduction of total cholesterol level is observed relative to the subject before administration of the composition.

In another aspect, the invention provides a method for reducing triglyceride levels in a subject comprising administering to a subject in need thereof an effective amount of a composition comprising a polar solvent soluble extract from Ortanique peel, wherein the reduction of triglyceride levels is observed relative to the subject before administration of the composition.

In one or more embodiments, the polar solvent is methanol.

In one or more embodiments, administration of the composition to the subject also results in an increase in HDL cholesterol level in the subject relative to the subject before administration of the composition.

In some embodiments, the subject is a human.

In one or more embodiments, the composition is suitable for oral administration.

In one or more embodiments, the extract comprises at least about 60% polymethoxylated flavones by weight.

In one or more embodiments, the extract comprises six different polymethoxylated flavones.

In one or more embodiments, the six polymethoxlylated flavones are nobiletin, sinensetin, tangeretin, heptamethoxyflavone, hexamethyl-o-quercetagetin, and tetramethylscutellarein.

In one or more embodiments, the extract comprises about 15-21% nobiletin, about 14.5-20.5% tetramethylscutellarein, about 4-10% sinensetin, about 13-19% tangeretin, about 0.3-2.3% hexamethyl-o-quercetagetin, and about 0.5-3.5% heptamethoxyflavone by weight.

In one or more embodiments, the extract comprises about 18% nobiletin, about 17.5% tetramethylscutellarein, about 7% sinensetin, about 16% tangeretin, about 1.3% hexamethyl-o-quercetagetin, and about 2% heptamethoxyflavone by weight.

In one aspect, the invention provides a method for reducing LDL cholesterol level in a subject comprising administering to a subject in need thereof an effective amount of a composition comprising substantially similar amounts of tetramethylscutellarein and nobiletin by weight, wherein the reduction of total cholesterol level is observed relative to the subject before administration of the composition.

In one or more embodiments, the composition comprises about 16-19% tetramethylscutellarein and about 16-19% nobiletin by weight.

In one or more embodiments, the composition comprises about 17.5% tetramethylscutellarein and about 18% nobiletin by weight.

In one or more embodiments, administration of the composition to the subject also results in an increase in HDL cholesterol level in the subject relative to the subject before administration of the composition.

In one or more embodiments, administration of the composition to the subject also results in a decrease in total cholesterol level in the subject relative to the subject before administration of the composition.

In one aspect, the invention provides a composition comprising substantially similar amounts of tetramethylscutellarein and nobiletin by weight, wherein the combined amount of tetramethylscutellarein and nobiletin is less than about 60% of the composition by weight.

In one or more embodiments, the composition comprises about 14-21% of each of tetramethylscutellarein and nobiletin by weight.

In some embodiments, the composition further comprises sinensetin, tangeretin, heptamethoxyflavone, and hexamethyl-o-quercetagetin.

In one or more embodiments, the composition comprises about 15-21% nobiletin, about 14.5-20.5% tetramethylscutellarein, about 4-10% sinensetin, about 13-19% tangeretin, about 0.3-2.3% hexamethyl-o-quercetagetin, and about 0.5-3.5% heptamethoxyflavone by weight.

In one or more embodiments, the composition comprises about 18% nobiletin, about 17.5% tetramethylscutellarein, about 7% sinensetin, about 16% tangeretin, about 1.3% hexamethyl-o-quercetagetin, and about 2% heptamethoxyflavone by weight.

In one or more embodiments, the composition comprises substantially similar amounts of tetramethylscutellarein, nobiletin and tangeretin by weight, wherein the combined amount of tetramethylscutellarein, nobiletin and tangeretin is less than about 60% of the composition by weight.

In one aspect, the invention provides a pharmaceutical formulation comprising: (a) a pharmaceutically acceptable carrier or vehicle; and (b) an effective amount of a composition of the invention.

In another aspect, the invention provides a pharmaceutical formulation comprising: (a) a pharmaceutically acceptable carrier or vehicle; and (b) an effective amount of a polar solvent soluble extract from Ortanique peel.

In one or more embodiments, the extract is methanol soluble.

5. BRIEF DESCRIPTION OF THE DRAWINGS

The invention is described with reference to the following FIGURE, which is presented for purposes of illustration only and which is not intending to be limiting of the invention.

FIG. 1 is a representation of the effects of Ortanique peel extract on HMG-CoA Reductase activity in (a) control rats fed a normal diet; (b) rats fed a diet with Ortanique peel extract; (c) diet-induced hypercholesterolemic rats fed a normal diet; (d) diet-induced hypercholesterolemic rats fed a diet with Ortanique peel extract; and (e) diet-induced hypercholesterolemic rats fed a diet with niacin.

6. DETAILED DESCRIPTION OF THE INVENTION

6.1 Definitions and Abbreviations

A "polymethoxylated flavone" or "PMF" is a flavone substituted with methoxy groups, for example, with 2, 3, 4, 5, 6, 7 or 8 methoxy groups and optionally substituted with one or more hydroxy groups, for example, 1, 2 or 3 hydroxy groups. Polymethoxylated flavones are almost exclusively found in citrus fruits with a specific characteristic distribution for each variety. Illustrative polymethoxylated flavones include, but are not limited to: (a) 5,6,7,8,3',4'-hexamethoxyflavone (nobiletin); (b) 5,6,7,3',4'-pentamethoxyflavone (sinensetin); (c) 5,6,7,8,4'-pentamethoxyflavone (tangeretin); (d) 3,5,6,7,8,3',4'-heptamethoxyflavone (heptamethoxyflavone); (e) 3,5,7,8,3',4'-hexamethoxyflavone (hexamethyl-o-quercetagetin); (f) 5,6,7,4'-tetramethoxyflavone (tetramethylscutellarein); (g) 5-hydroxy-6,7,8,3',4'-pentamethoxyflavone; (h) 5,7,8,3',4'-pentamethoxyflavone; (i) 7-hydroxy-3,5,6,7,3',4'-hexamethoxyflavone; (j) 5-hydroxy-3,6,7,8,3',4'-hexamethoxyflavone; (k) 5,6,7,3',4',5'-hexamethoxyflavone; and (l) 5,7,3',4'-tetramethoxyflavone.

Two parameter values are "substantially similar" if they have values within ±10% of each other. The parameter values can be expressed as absolute values (e.g., weight) or as relative values (e.g., percentage).

As used herein, "about" means ±10% of the value that follows it.

A "polar solvent" is a protic or aprotic polar solvent. Aprotic polar solvents include, but are not limited to, 1,4-dioxane, tetrahydrofuran, dichloromethane, acetonitrile, dimethylformamide, dimethyl sulfoxide. Protic polar solvents include, but are not limited to, acetic acid, n-butanol, isopropanol, n-propanol, ethanol, methanol, and formic acid.

As used herein, "PMF-ORT" is the Ortanique peel extract described herein.

As used herein, a solid is "soluble" in a given solvent if the solid has solubility of at least 0.1 g/L in the solvent under desired conditions, such as temperature, pressure, and pH.

The following abbreviations are used herein and have the indicated definitions: LDL is low-density lipoprotein, HDL is high-density lipoprotein, VLDL is very-low-density lipoprotein, DMSO is dimethyl sulfoxide, PMF is polymethoxylated flavone, MDA is malondialdehyde, HPLC is High Performance Liquid Chromatography, HMG-CoA reductase is 3-hydroxy-3-methyl-glutaryl-CoA reductase, and U is unit.

6.2 Ortanique Citrus Fruit

The Ortanique fruit, a type of tangor, is a Jamaican hybrid between tangerine (*Citrus reticulata*) and sweet orange (*Citrus sinensis*). The name "Ortanique" is derived from a combination of the words "orange," "tangerine," and "unique" and is indigenous to Jamaica. Ortanique fruit is grown commercially in Jamaica. The Ortanique grows well in hot, dry weather on shallow bauxite soil at an elevation of about 2,500 feet. In Jamaica, Ortanique is cultivated on approximately 1550 acres and over 270,000 boxes of fresh fruits are produced annually, the majority of which (over 90%) is consumed locally.

The Ortanique peel contains a high percentage by weight of polymethoxylated flavones, and further contains a unique combination of six known polymethoxylated flavones, namely, nobiletin, sinensetin, tangeretin, heptamethoxyflavone, hexamethyl-o-quercetagetin, and tetramethylscutellarein. The Ortanique peel contains a higher overall percentage by weight of polymethoxylated flavones than either the tangerine peel or the sweet orange peel. Tangerine peel and sweet orange peel were previously reported to contain the highest percentage by weight of polymethoxylated flavones.

6.3 Compositions of Ortanique Peel Extract (PMF-ORT)

In some embodiments, the Ortanique peel extract contains over 40%, over 50%, over 60% or over 70% of polymethoxylated flavones by weight. By weight, the Ortanique peel extract can contain about 15-21% nobiletin, about 14.5-20.5% tetramethylscutellarein, about 4-10% sinensetin, about 13-19% tangeretin, about 0.3-2.3% hexamethyl-o-quercetagetin, and about 0.5-3.5% heptamethoxyflavone.

In a specific embodiment, the Ortanique peel extract contains the following approximate weight percentages (w/w) of polymethoxylated flavones: 18% nobiletin, 17.5% tetramethylscutellarein, 7% sinensetin, 16% tangeretin, 1.3% hexamethyl-o-quercetagetin, and 2% heptamethoxyflavone. This distribution of polymethoxylated flavones is unique to the Ortanique peel, and is believed to have an important role in the potency of the Ortanique peel extract (PMF-ORT). Of course, the percentages of polymethoxylated flavones listed above can vary by as much as a few percent from the values listed above Compositions described herein and extracts from the Ortanique peel can comprise substantially similar amounts of tetramethylscutellarein and nobiletin by weight. This amount can be, for example, 14-21%, 15-20%, 16-19%, or 17-18% for each of tetramethylscutellarein and nobiletin. In a specific embodiment, the composition comprises about 18% nobiletin and about 17.5% tetramethylscutellarein by weight.

In some embodiments, the composition comprises substantially similar amounts of tetramethylscutellarein, nobiletin, and tangeretin by weight. This amount can be 14-21%, 15-20%, 16-19% or 17-18% for each of tetramethylscutellarein, nobiletin, and tangeretin. In a specific embodiment, the composition comprises about 18% nobiletin, about 17.5% tetramethylscutellarein, and about 16% tangeretin by weight.

6.4 Method of Making Ortanique Peel Extract (PMF-ORT)

Because only the peel of the Ortanique is used, PMF-ORT can be made from Ortanique fruit that has been used for juice production. The juice production results in large quantities of the peel and other byproducts which end up being discarded and can even cause environmental problems.

Ortanique peel extract (PMF-ORT) can be made by the following process. First, Ortanique fruits are peeled, and the peel is dried. The dried peel is then milled to a fine powder. Extraction of the polymethoxylated flavones from the peel is performed by soaking the peel in a polar solvent such as methanol. The extract is then filtered and the solvent is evaporated. The resultant solids are dried to provide the Ortanique peel extract (PMF-ORT).

In some embodiments, the Ortanique peel extract contains over 60% polymethoxylated flavones by weight. This concentration is greater than the concentration of polymethoxylated flavones in tangerine peel extract or sweet orange peel extract. By weight, the Ortanique peel extract can contain the following approximate percentages (w/w) of polymethoxylated flavones: 18% nobiletin, 17.5% tetramethylscutellarein, 7% sinensetin, 16% tangeretin, 1.3% hexamethyl-o-quercetagetin, and 2% heptamethoxyflavone. This distribution of polymethoxylated flavones is unique to the Ortanique peel, and is believed to have an important role in the potency of the Ortanique peel extract (PMF-ORT). Of course, the percentages of polymethoxylated flavones listed above can vary by as much as a few percent from the values listed above. Thus, it is contemplated that the Ortanique peel extract can contain about 15-21% nobiletin, about 14.5-20.5% tetramethylscutellarein, about 4-10% sinensetin, about 13-19% tangeretin, about 0.3-2.3% hexamethyl-o-quercetagetin, and about 0.5-3.5% heptamethoxyflavone.

6.5 Methods of Using Ortanique Peel Extract

6.5.1 Methods for Treating Hypercholesterolemia

The Ortanique peel extract is useful for treatment or prevention of hypercholesterolemia. Accordingly, the invention provides methods for treating or preventing hypercholesterolemia in a subject, comprising administering to a subject in need of such treatment or such prevention an effective amount of Ortanique peel extract.

Experiments carried out on hypercholesterolemic rats indicated that the supplementation of the rats' diets with Ortanique peel extract resulted in statistically significant reductions in serum levels of total cholesterol and LDL cholesterol, as well as triglycerides, when compared to hypercholesterolemic rats fed normal food without supplementation and when compared to hypercholesterolemic rats fed food supplemented with niacin, a standard cholesterol reducing drug. Unexpectedly, the hypercholesterolemic rats fed Ortanique peel extract also experienced an elevation in serum HDL cholesterol levels compared to hypercholesterolemic rats fed normal food without supplementation and hypercholesterolemic rats fed food supplemented with niacin. This experimental data indicates that Ortanique peel extract is useful for reducing serum levels of total cholesterol in a subject, reducing serum levels of LDL cholesterol in a subject, reducing serum levels of triglycerides in a subject, and increasing serum levels of HDL cholesterol in a subject.

Unexpectedly, the Ortanique peel extract is more effective in treating hypercholesterolemia compared to peel extracts from other citrus fruits. For instance, a study performed using tangerine peel extract in hypercholesterolemic hamster diets resulted in significantly reduced serum total cholesterol and serum LDL cholesterol levels, and tended to reduce serum triacylglycerols, but resulted in no increase in serum HDL levels. By contrast, supplementation of diet with the Ortanique peel extract resulted in even greater reduction in total serum cholesterol, serum LDL cholesterol, and serum triglyceride levels, and further resulted in an increase in serum HDL levels. (See Kurowska and Manthey, Hypolipidemic Effects and Absorption of Citrus Polymethoxylated Flavones in Hamsters with Diet-Induced Hypercholesterolemia, *J. Agric. Food Chem.* 52: 2879-2886 (2004)).

6.5.2 Methods for Reducing LDL Cholesterol Levels

The Ortanique peel extract is useful for reducing LDL cholesterol levels in a subject in need thereof. Accordingly, the invention provides methods for reducing LDL cholesterol levels in a subject, comprising administering to a subject in need of such reduction an effective amount of Ortanique peel extract. Experiments carried out on hypercholesterolemic rats indicated that the supplementation of the rats' diets with Ortanique peel extract resulted in significant reductions in serum levels of LDL cholesterol compared to hypercholesterolemic rats fed normal food without supplementation and hypercholesterolemic rats fed food supplemented with niacin, a standard cholesterol reducing drug. This experimental data indicates that Ortanique peel extract is useful for reducing serum levels of LDL cholesterol in a subject.

6.5.3 Methods for Reducing Triglyceride Levels

The Ortanique peel extract is useful for reducing triglyceride levels in a subject in need thereof. Accordingly, the invention provides methods for reducing triglyceride levels in a subject, comprising administering to a subject in need of such reduction an effective amount of Ortanique peel extract. Experiments carried out on hypercholesterolemic rats indicated that the supplementation of the rats' diets with Ortanique peel extract resulted in significant reductions in serum levels of triglycerides compared to hypercholesterolemic rats fed normal food without supplementation and hypercholesterolemic rats fed food supplemented with niacin, a standard cholesterol reducing drug. This experimental data indicates that Ortanique peel extract is useful for reducing serum levels of triglycerides in a subject.

6.5.4 Methods for Increasing HDL Cholesterol Levels

The Ortanique peel extract is useful for increasing HDL cholesterol levels in a subject in need thereof. Accordingly, the invention provides methods for increasing HDL cholesterol levels in a subject, comprising administering to a subject in need of such reduction an effective amount of Ortanique peel extract. Experiments carried out on hypercholesterolemic rats indicated that the supplementation of the rats' diets with Ortanique peel extract resulted in significant increases in serum levels of HDL cholesterol compared to hypercholesterolemic rats fed normal food without supplementation and hypercholesterolemic rats fed food supplemented with niacin, a standard cholesterol reducing drug. This experimental data indicates that Ortanique peel extract is useful for reducing serum levels of triglycerides in a subject.

Furthermore, with respect to HDL cholesterol levels, the Ortanique peel extract yields different, unexpected results when compared to peel extracts from other citrus fruits. For instance, a study performed using tangerine peel extract in hypercholesterolemic hamster diets resulted in no increase in serum HDL cholesterol levels. By contrast, the Ortanique peel extract study resulted in a significant increase in serum HDL cholesterol levels. (See Kurowska and Manthey, Hypolipidemic Effects and Absorption of Citrus Polymethoxylated Flavones in Hamsters with Diet-Induced Hypercholesterolemia, *J. Agric. Food Chem.* 52: 2879-2886 (2004)).

6.5.5 Methods for Administering Ortanique Peel Extract

The Ortanique peel extract can be administered to subjects in a variety of ways. In one embodiment, the Ortanique peel extract is administered orally to a subject, e.g., in the form of a tablet. The tablet can comprise Ortanique peel extract combined, in appropriate quantities, with a suitable medium to form a tablet. In another embodiment, the Ortanique peel extract is administered orally to a subject in the form of a capsule. The capsule can comprise Ortanique peel extract encapsulated in a standard ingestible capsule.

The Ortanique peel extract can also be incorporated into various foods and beverages, thus forming a nutraceutical. Examples of suitable beverages include, but are not limited to, fruit juices and sodas (e.g., colas). Examples of suitable foods include, but are not limited to, chocolates, snacks, confectionery, pizza, foods made from cereal flour (e.g., breads, cakes, crackers, cookies, biscuits, and noodles), and seasonings and spices used to prepare meat.

The Ortanique peel extract can be formulated into pharmaceutical compositions together with a pharmaceutically acceptable carrier or vehicle for oral administration in solid or liquid form, or for intravenous, intramuscular, or subcutaneous administration.

Pharmaceutically acceptable carriers for oral administration include capsules, tablets, pills, powders, troches, and granules. In the case of solid dosage forms, the pharmaceutically acceptable carrier can comprise at least one inert diluent such as sucrose, lactose or starch. Such pharmaceutically acceptable carriers can also comprise additional substances other than diluents, e.g., lubricating agents such as magnesium stearate. In the case of capsules, tablets, troches and pills, the pharmaceutically acceptable carrier can also comprise buffering agents. Carriers, such as tablets, pills and granules, can be prepared with enteric coatings on the surfaces of the tablets, pills or granules. Alternatively, the enteric coated compounds can be pressed into tablets, pills, or granules.

Pharmaceutically acceptable carriers include liquid dosage forms for oral administration, e.g., emulsions, solutions, suspensions, syrups and elixirs containing inert diluents commonly used in the art, such as water. Besides such inert diluents, compositions can also include adjuvants, such as wetting agents, emulsifying and suspending agents, and sweetening, flavoring agents.

Pharmaceutical compositions of the invention for parenteral administration comprise product according to the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Pharmaceutically acceptable carriers for intravenous administration include solutions containing pharmaceutically acceptable salts or sugars. Pharmaceutically acceptable carriers for intramuscular or subcutaneous injection include salts, oils, or sugars.

Furthermore, carriers such as solvents, water, buffers, alkanols, cyclodextrins and aralkanols can be used. Other auxiliary, non-toxic agents may be included, for example, polyethylene glycols or wetting agents.

The pharmaceutically acceptable carriers and compositions of the invention are formulated into unit dosage forms for administration to the patients. The dosage levels of active ingredient (i.e., Ortanique peel extract) in the unit dosage may be varied so as to obtain an amount of active ingredient that is effective to achieve a therapeutic effect in accordance with the desired method of administration. The selected dosage level therefore mainly depends upon the nature of the active ingredient, the route of administration, and the desired duration of treatment. If desired, the unit dosage can be such that the daily requirement for the Ortanique peel extract product is in one dose, or divided among multiple doses for administration, e.g., two, three, or four times per day.

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below. A number of references have been cited, the entire disclosures of which have been incorporated herein in their entirety.

7. EXAMPLES

7.1 Example 1

Preparation of Ortanique Peel Extract

Jamaican indigenous Ortanique fruit was harvested. The fruits were thoroughly washed and peeled. The peel was dried in the sun for 4-8 days and milled to fine powder using a commercial blender. The powdered peel was then extracted with reagent grade methanol (3×500 mL) at room temperature for 24 hours with constant stirring. The mixture was filtered, and the filtrate was evaporated via rotary evaporation.

The resulting solids were first air-dried, then further dried in an oven at 70° C. to provide the Ortanique peel extract (PMF-ORT) as a solid.

7.2 Example 2

Determination of the Composition of Ortanique Peel Extract

The Ortanique peel extract was characterized using reverse-phase high performance liquid chromatography (HPLC) with UV detection. Elution was carried out in the gradient mode, using a ternary mobile phase. The polymethoxylated flavone components of Ortanique citrus peel extract and their respective quantities were determined using this method.

The Ortanique PMF extract was found to contain the following combination of six different PMFs: nobiletin (5,6,7,8,3',4'-hexamethoxyflavone), sinensetin (5,6,7,3',4'-pentamethoxyflavone), tangeretin (5,6,7,8,4'-pentamethoxyflavone), heptamethoxyflavone (3,5,6,7,8,3',4'-heptamethoxyflavone), hexamethyl-o-quercetagetin (3,5,7,8,3', 4'-hexamethoxyflavone) and tetramethylscutellarein (5,6,7,4'-tetramethoxyflavone), in the following proportions by weight: 18% nobiletin, 17.5% tetramethylscutellarein, 7% sinensetin, 16% tangeretin, 1.3% hexamethyl-o-quercetagetin, and 2% heptamethoxyflavone.

7.3 Example 3

Determination of Efficacy of Ortanique Peel Extract

To determine the effects of Ortanique peel extract on various cholesterol levels, the following animal model experiments were carried out.

Thirty Sprague-Dawley rates were divided into five groups. Group 1 consisted of healthy rats fed a normal diet. Group 2 consisted of diet-induced hypercholesterolemic rats. Group 3 consisted of healthy rats fed Ortanique peel extract. Group 4 consisted of diet-induced hypercholesterolemic rats fed Ortanique peel extract. Group 5 consisted of diet-induced hypercholesterolemic rats fed niacin, a common cholesterol reducing drug. The normal diet consisted of normal rat chow. Rats were made hypercholesterolemic by being fed a diet consisting of 1% cholic acid and 4% cholesterol mixed with the normal rat chow. Rats that were fed Ortanique peel extract were fed normal rat chow mixed with Ortanique peel extract that consisted of 1.5% Ortanique peel extract by weight. Rats were fed their respective diets for forty-nine (49) days, after which they were sacrificed. Blood serum and organs were obtained for analyses and several biochemical parameters were tested.

Hypercholesterolemic rats fed diets supplemented with Ortanique peel extract (Group 4) exhibited significantly lower total serum cholesterol concentration ($3.11 \pm 0.10$ mmol/l; $p<0.05$) compared to Group 2 hypercholesterolemic control rats ($5.49 \pm 0.49$ mmol/l) and Group 5 hypercholesterolemic rats fed with niacin ($4.57 \pm 0.44$ mmol/l).

Hypercholesterolemic rats fed diets supplemented with Ortanique peel extract (Group 4) also exhibited reduced serum LDL cholesterol concentration ($0.97 \pm 0.24$ mmol/l; $p<0.05$) compared to Group 2 hypercholesterolemic control rats ($3.12 \pm 0.53$ mmol/l) and Group 5 hypercholesterolemic rats fed with niacin ($2.36 \pm 0.27$ mmol/l).

Hypercholesterolemic rats fed diets supplemented with Ortanique peel extract (Group 4) further exhibited reduced serum triglyceride concentration ($3.45 \pm 0.29$ mmol/l, $p<0.05$) compared to Group 2 hypercholesterolemic control rats ($4.51 \pm 0.64$ mmol/l) and Group 5 hypercholesterolemic rats fed with niacin ($3.97 \pm 0.53$ mmol/l).

Hypercholesterolemic rats fed diets supplemented with Ortanique peel extract (Group 4) also exhibited increased serum HDL cholesterol concentration ($0.58 \pm 0.05$ mmol/l; $p<0.05$) compared to Group 2 hypercholesterolemic control rats ($0.32 \pm 0.05$ mmol/l) and Group 5 hypercholesterolemic rats fed with niacin ($0.39 \pm 0.07$ mmol/l).

In addition, hypercholesterolemic rats fed diets supplemented with Ortanique peel extract (Group 4) exhibited reduced hepatic activity of HMG-CoA Reductase, the enzyme that catalyses the rate limiting step in cholesterol synthesis, compared to Group 2 hypercholesterolemic control rats and Group 5 hypercholesterolemic rats fed with niacin. Thus, supplementation of the diets with Ortanique peel extract inhibited the hepatic activity of the rate limiting enzyme involved in cholesterol synthesis—HMG-CoA Reductase, as seen in FIG. 1. Different letter superscripts (above each column) denote significant differences between values ($p<0.05$).

7.4 Example 4

Effect of Jamaican Ortanique Peel Polymethoxylated Flavones on Liver And Kidney Function in Diet-Induced Hypercholesterolemic Rats Malonedialdehyde (MDA) level was used as a measure of lipid peroxidation. Hypercholesterolemic rats fed diets supplemented with PMF-ORT were found to have significantly reduced lipid peroxide levels ($650.86 \pm 128.28$ nmol MDA/g wet weight; $p<0.05$) in their liver compared to hypercholesterolemic control ($3,381.56 \pm 954$ nmol MDA/g wet weight) and hypercholesterolemic rats fed niacin ($1,316.07 \pm 201.72$ nmol MDA/g wet wt). No significant difference was however observed in the lipid peroxide levels in the kidneys of hypercholesterolemic rats fed PMF-ORT ($1,243.03 \pm 421.16$ nmol MDA/g wet weight) when compared to the hypercholesterolemic control ($1,363.70 \pm 440.9$ nmol MDA/g wet weight) as well as hypercholesterolemic rats fed niacin ($1,127.28 \pm 354.65$ nmol MDA/g wet weight), respectively. Liver function analyses supported results obtained from lipid peroxidation analysis. Reduced activities in serum aspartate aminotransferase and alkaline phosphatase were found in hypercholesterolemic rats whose diets were supplemented with PMF-ORT ($69 \pm 3.34$ and $100 \pm 9.20$ U/L) when compared to hypercholesterolemic control ($118 \pm 9.18$ and $132.60 \pm 15.71$ U/L) and hypercholesterolemic rats fed niacin ($136.40 \pm 27.34$ and $80.6 \pm 4.45$ U/L), respectively. There were however, no significant differences between the levels of serum creatinine or urea among the groups.

As indicated in Example 4, supplementation of the diets of hypercholesterolemic rats with Jamaican Ortanique peel extract (PMF-ORT) resulted in statistically significant reductions in lipid peroxide levels in organs as well as reductions in biochemical indicators of kidney and liver function compared with untreated hypercholesterolemic rats.

7.5 Example 5

Effect of Jamaican Ortanique Peel Polymethoxylated Flavones on Activities of Endogenous Antioxidant Enzymes in Diet-Induced Hypercholesterolemic Rats Supplementation of the diets with PMF-ORT resulted in reductions in the activities of endogenous antioxidant enzymes (glutathione reductase, glutathione peroxidase, glutathione transferase and catalase) in the liver, kidney, brain, spleen, and heart of rats.

Table 1 shows activity of glutathione reductase in the liver, kidney, brain, spleen, and heart of rats.

TABLE 1

| Glutathione Reductase Activity (nmol/min/mg protein)* | | | | | |
|---|---|---|---|---|---|
| Group | Heart | Liver | Kidney | Spleen | Brain |
| Normal control | 14.14 ± 0.60$^a$ | 29.28 ± 2.0$^a$ | 10.44 ± 0.51$^a$ | 23.94 ± 4.86$^b$ | 25.52 ± 0.27$^a$ |
| Hyp. Control | 20.08 ± 0.18$^a$ | 41.05 ± 3.45$^{ab}$ | 16.71 ± 1.52$^a$ | 43.62 ± 3.67$^a$ | 24.05 ± 1.69$^a$ |
| Normal Fed PMFs | 21.44 ± 0.55$^a$ | 30.62 ± 5.06$^a$ | 4.83 ± 0.12$^a$ | 31.00 ± 2.01$^{ab}$ | 16.27 ± 3.92$^a$ |
| Hyp. Fed PMFs | 20.23 ± 0.95$^a$ | 18.20 ± 1.63$^a$ | 7.99 ± 0.11$^a$ | 16.56 ± 3.12$^b$ | 11.45 ± 2.25$^a$ |
| Hyp. Fed Niacin | 12.53 ± 0.85$^a$ | 61.23 ± 5.45$^{ab}$ | 12.36 ± 0.10$^a$ | 49.48 ± 3.32$^a$ | 14.95 ± 1.67$^a$ |

*Different letter superscripts (in each column) denote significant differences between values ($p < 0.05$).

Table 2 shows activity of glutathione peroxidase in the liver, kidney, brain, spleen. and heart of rats.

TABLE 2

| Glutathione Peroxidase Activity (nmol/min/mg protein)* | | | | | |
|---|---|---|---|---|---|
| Group | Heart | Liver | Kidney | Spleen | Brain |
| Normal control | 4.57 ± 0.94$^a$ | 1.30 ± 0.27$^a$ | 5.92 ± 0.71$^a$ | 6.14 ± 0.42$^a$ | 0.49 ± 0.086$^a$ |
| Hyp. Control | 9.54 ± 1.81$^a$ | 2.54 ± 0.76$^a$ | 5.88 ± 1.33$^a$ | 25.95 ± 5.32$^b$ | 1.63 ± 0.11$^b$ |
| Normal Fed PMFs | 7.36 ± 0.81$^a$ | 0.81 ± 0.027$^a$ | 5.31 ± 0.75$^a$ | 10.85 ± 1.22$^a$ | 0.72 ± 0.02$^a$ |
| Hyp. Fed PMFs | 5.61 ± 0.22$^a$ | 1.18 ± 0.33$^a$ | 4.86 ± 1.05$^a$ | 1.18 ± 0.33$^a$ | 0.54 ± 0.018$^a$ |
| Hyp. Fed Niacin | 5.14 ± 0.63$^a$ | 0.95 ± 0.03$^a$ | 3.35 ± 1.30$^a$ | 0.21 ± 0.034$^a$ | 0.59 ± 0.18$^a$ |

*Different letter superscripts (in each column) denote significant differences between values ($p < 0.05$).

Table 3 shows activity of glutathione transferase in the liver, kidney, brain, spleen, and heart of rats.

TABLE 3

| Glutathione Transferase Activity (nmol/min/mg protein)* | | | | | |
|---|---|---|---|---|---|
| Group | Heart | Liver | Kidney | Spleen | Brain |
| Normal control | 0.21 ± 0.012$^a$ | 1.46 ± 0.55$^a$ | 0.089 ± 0.006$^a$ | 0.077 ± 0.016$^a$ | 0.25 ± 0.03$^a$ |
| Hyp. Control | 0.22 ± 0.038$^a$ | 3.04 ± 0.68$^a$ | 0.53 ± 0.18$^b$ | 0.12 ± 0.033$^b$ | 0.44 ± 0.05$^b$ |
| Normal Fed PMFs | 0.19 ± 0.013$^a$ | 1.50 ± 0.41$^a$ | 0.16 ± 0.03$^a$ | 0.019 ± 0.002$^a$ | 0.28 ± 0.046$^a$ |
| Hyp. Fed PMFs | 0.18 ± 0.011$^a$ | 2.49 ± 0.17$^a$ | 0.14 ± 0.029$^a$ | 0.067 ± 0.018$^a$ | 0.26 ± 0.011$^a$ |
| Hyp. Fed Niacin | 0.21 ± 0.011$^a$ | 2.37 ± 0.42$^a$ | 0.20 ± 0.05$^b$ | 0.16 ± 0.07$^b$ | 0.28 ± 0.04$^a$ |

*Different letter superscripts (in each column) denote significant differences between values ($p < 0.05$).

Table 4 shows activity of catalase in the liver, kidney, brain, spleen and heart of rats.

TABLE 4

| Catalase Activity (nmol/min/mg protein)* | | | | | |
|---|---|---|---|---|---|
| Group | Heart | Liver | Kidney | Spleen | Brain |
| Normal control | 10.50 ± 5.54$^a$ | 5.22 ± 0.22$^a$ | 5.82 ± 0.047$^a$ | 172.00 ± 10.45$^a$ | 2.95 ± .015$^a$ |
| Hyp. Control | 216.98 ± 0.14$^b$ | 114.21 ± 9.21$^b$ | 15.45 ± 0.84$^b$ | 223.87 ± 28.56$^a$ | 21.49 ± 1.40$^b$ |
| Normal Fed PMFs | 19.40 ± 10.50$^a$ | 2.37 ± 0.37$^a$ | 4.38 ± 0.21$^a$ | 158.21 ± 19.68$^a$ | 3.18 ± 0.09$^a$ |
| Hyp. Fed PMFs | 3.09 ± 0.09$^a$ | 1.00 ± 0.04$^a$ | 8.48 ± 0.32$^a$ | 288.74 ± 9.67$^a$ | 1.13 ± 0.04$^a$ |
| Hyp. Fed Niacin | 18.07 ± 1.33$^a$ | 19.94 ± 1.25$^a$ | 5.51 ± 0.69$^a$ | 329.74 ± 35.02$^a$ | 2.23 ± 0.04$^a$ |

*Different letter superscripts (in each column) denote significant differences between values ($p < 0.05$).

As indicated in Tables 1-4, supplementation of the diets of hypercholesterolemic with PMF-ORT resulted in statistically significant reductions activities of antioxidant enzymes in liver, kidney, brain, spleen, and heart.

What is claimed is:

1. A method for increasing HDL cholesterol level in a subject comprising administering to a subject in need thereof an effective amount of a composition comprising a polar solvent soluble extract from Ortanique peel, wherein the extract comprises at least about 40% polymethoxylated flavones by weight, and wherein the increase of HDL cholesterol level is observed relative to the subject before administration of the composition.

2. The method of claim 1, wherein the polar solvent is methanol.

3. The method of claim 1, wherein the composition is suitable for oral administration.

4. The method of claim 1, wherein the extract comprises at least about 60% polymethoxylated flavones by weight.

5. The method of claim 1, wherein the extract comprises six different polymethoxylated flavones.

6. The method of claim 5, wherein the six polymethoxlylated flavones are nobiletin, sinensetin, tangeretin, heptamethoxyflavone, hexamethyl-o-quercetagetin, and tetramethylscutellarein.

7. The method of claim 6, wherein the extract comprises about 15-21% nobiletin, about 14.5-20.5% tetramethylscutellarein, about 4-10% sinensetin, about 13-19% tangeretin, about 0.3-2.3% hexamethyl-o-quercetagetin, and about 0.5-3.5% heptamethoxyflavone by weight.

8. The method of claim 7, wherein the extract comprises about 18% nobiletin, about 17.5% tetramethylscutellarein, about 7% sinensetin, about 16% tangeretin, about 1.3% hexamethyl-o-quercetagetin, and about 2% heptamethoxyflavone by weight.

* * * * *